(12) United States Patent
Seiki et al.

(10) Patent No.: US 6,753,352 B2
(45) Date of Patent: Jun. 22, 2004

(54) METHOD FOR MANUFACTURING SYNTHESIS GAS AND METHOD FOR MANUFACTURING METHANOL

(75) Inventors: Yoshio Seiki, Hiroshima-ken (JP); Tetsuya Imai, Hiroshima-ken (JP); Kazuto Kobayashi, Hiroshima-ken (JP); Hiroyuki Osora, Hiroshima-ken (JP); Chie Kuwada, Hiroshima-ken (JP); Kazuhiro Morita, Tokyo (JP); Shuichi Miyamoto, Tokyo (JP)

(73) Assignees: Mitsubishi Heavy Industries, Ltd., Tokyo (JP); Mitsubishi Gas Chemical Company, Inc., Tokyo (JP)

(*) Notice: Subject to any disclaimer, the term of this patent is extended or adjusted under 35 U.S.C. 154(b) by 4 days.

(21) Appl. No.: 10/197,423

(22) Filed: Jul. 18, 2002

(65) Prior Publication Data
US 2003/0022948 A1 Jan. 30, 2003

(30) Foreign Application Priority Data

Jul. 19, 2001 (JP) .................................. 2001-219930

(51) Int. Cl.$^7$ .......................... C07C 27/00; C07C 1/02; C01B 3/24; C01B 31/18
(52) U.S. Cl. ...................... 518/702; 518/700; 518/704; 252/373; 423/650; 423/418.2
(58) Field of Search ................................. 518/700, 702, 518/704; 252/373; 423/650, 418.2

(56) References Cited

U.S. PATENT DOCUMENTS 6,218,439 B1    4/2001    Kobayashi et al.

FOREIGN PATENT DOCUMENTS

| EP | 1 008 577 | 6/2000 |
| GB | 2 213 817 | 8/1989 |
| JP | 1-180841 | 7/1989 |

*Primary Examiner*—J. Parsa
(74) *Attorney, Agent, or Firm*—Oblon, Spivak, McClelland, Maier & Neustadt, P.C.

(57) ABSTRACT

There is disclosed a method of manufacturing a synthesis gas comprising reacting hydrocarbons with water vapor in a reformer to produce a synthesis gas containing hydrogen, carbon monoxide and carbon dioxide, recovering carbon dioxide from combustion exhaust gas which has been discharged from the reformer by a carbon dioxide recovery apparatus provided with a carbon dioxide absorption tower and with a carbon dioxide-absorbing liquid regenerating tower, and feeding the carbon dioxide thus recovered, as a component of raw gas, to the upstream side and/or the downstream side of the reformer. The hot synthesis gas produced in the reformer is utilized as a heat source for regenerating a carbon dioxide-absorbing liquid in the carbon dioxide-absorbing liquid regenerating tower of the carbon dioxide recovery apparatus.

10 Claims, 2 Drawing Sheets

METHOD FOR MANUFACTURING SYNTHESIS GAS AND METHOD FOR MANUFACTURING METHANOL

CROSS-REFERENCE TO RELATED APPLICATIONS

This application is based upon and claims the benefit of priority from the prior Japanese Patent Application No. 2001-219930, filed Jul. 19, 2001, the entire contents of which are incorporated herein by reference.

BACKGROUND OF THE INVENTION

1. Field of the Invention

This invention relates to a method of manufacturing a synthesis gas to be employed in the manufacture of methanol, in the manufacture of gasoline by means of GTL (Gas to Liquid) process, or in the manufacture of dimethyl ether, and also relates to a method of manufacturing methanol.

2. Description of the Related Art

A synthesis gas comprising hydrogen ($H_2$) and carbon monoxide (CO) is employed as a raw material for synthesizing methanol for example.

This synthesis gas is conventionally manufactured by a method wherein a gaseous hydrocarbon or a vaporized liquid hydrocarbon is allowed to react, by making use of a reformer, with water vapor in the presence of a nickel catalyst at a temperature ranging from 800 to 1000° C. to produce the synthesis gas. This synthesis gas comprises, as main components, hydrogen ($H_2$), carbon monoxide (CO) and carbon dioxide ($CO_2$).

In the meantime, Jpn. Pat. Appln. KOKAI Publication No. 1-180841 discloses one example of the method of manufacturing such a synthesis gas, wherein carbon dioxide existing in a combustion exhaust gas discharged from a reformer is recovered by a carbon dioxide recovery apparatus provided with a carbon dioxide absorption tower and with a carbon dioxide-absorbing liquid regenerating tower, and the carbon dioxide thus recovered is fed to the upstream side of the reformer and/or the downstream side of the reformer to obtain a synthesis gas having a desired molar ratio of $H_2/CO$ which is suitable for the synthesis of methanol.

However, as the quantity of carbon dioxide to be recovered by the carbon dioxide recovery apparatus is increased in the conventional method of manufacturing methanol, the quantity of heat required to be used in the carbon dioxide recovery apparatus is caused to increase correspondingly, thus inviting a shortage of heating sources and hence increasing the manufacturing cost of methanol.

BRIEF SUMMARY OF THE INVENTION

An object of the present invention is to provide a method of manufacturing a synthesis gas having a suitable molar ratio of $H_2/(CO+CO_2)$ for the synthesis of methanol, wherein the waste heat of hot synthesis gas produced in a reformer is effectively utilized as a heat source for a carbon dioxide recovery apparatus, thereby making it possible to cope with any increase in heat quantity to be used in the carbon dioxide recovery apparatus.

Another object of the present invention is to provide a method of manufacturing methanol, which is capable of producing a synthesis gas having a suitable molar ratio of $H_2/(CO+CO_2)$ for the synthesis of methanol, and also capable of effectively utilizing the waste heat of hot synthesis gas produced in a reformer gas a heat source for a carbon dioxide recovery apparatus as well as a heat source for a distillation apparatus, thereby making it possible to minimize the consumption of energy.

According to the present invention, there is provided a method of manufacturing a synthesis gas comprising: reacting hydrocarbons with water vapor (steam) in a reformer to produce a synthesis gas containing hydrogen, carbon monoxide and carbon dioxide; recovering carbon dioxide from combustion exhaust gas which has been discharged from the reformer by a carbon dioxide recovery apparatus provided with a carbon dioxide absorption tower and with a carbon dioxide-absorbing liquid regenerating tower; and feeding the carbon dioxide thus recovered, as a component of raw gas, to the upstream side and/or the downstream side of the reformer;

wherein the hot synthesis gas produced in the reformer is utilized as a heat source for regenerating a carbon dioxide-absorbing liquid in the carbon dioxide-absorbing liquid regenerating tower of the carbon dioxide recovery apparatus.

According to the present invention, there is also provided a method of manufacturing methanol comprising:

reacting hydrocarbons with water vapor (steam) in a reformer to thereby produce a synthesis gas containing hydrogen, carbon monoxide and carbon dioxide;

recovering carbon dioxide from combustion exhaust gas which has been discharged from the reformer by a carbon dioxide-recovering device provided with a carbon dioxide absorption tower and with a carbon dioxide-absorbing liquid regenerating tower;

feeding the carbon dioxide thus recovered, as a component of raw gas, to the upstream side and/or the downstream side of the reformer;

producing a crude methanol by introducing the synthesis gas into a methanol-synthesizing reactor; and distilling the crude methanol by making use of a distillation apparatus to produce a refined methanol;

wherein the hot synthesis gas produced in the reformer is utilized as a heat source for regenerating a carbon dioxide-absorbing liquid in the carbon dioxide-absorbing liquid regenerating tower, and the hot synthesis gas produced in the reformer is utilized as a heat source for the distillation apparatus.

It is preferable, in the method of manufacturing methanol according to the present invention, that the hot synthesis is permitted to pass through a heat exchanger of the carbon dioxide-absorbing liquid regenerating tower and through a heat exchanger of the distillation apparatus, thereby enabling the hot synthesis gas to undergo the heat exchange thereof. In particular, it is preferable that the distillation apparatus is provided with a first, a second and a third distillation towers each provided with a heat exchanger, thereby enabling the hot synthesis gas from the reformer to pass successively through the heat exchanger of the second distillation tower, the heat exchanger of the carbon dioxide-absorbing liquid regenerating tower, the heat exchanger of the third distillation tower, and the heat exchanger of the first distillation tower, thus enabling the hot synthesis gas to successively undergo the heat exchange thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Next, the methods of manufacturing methanol according to the present invention will be explained with reference to drawings.

Figure 1:
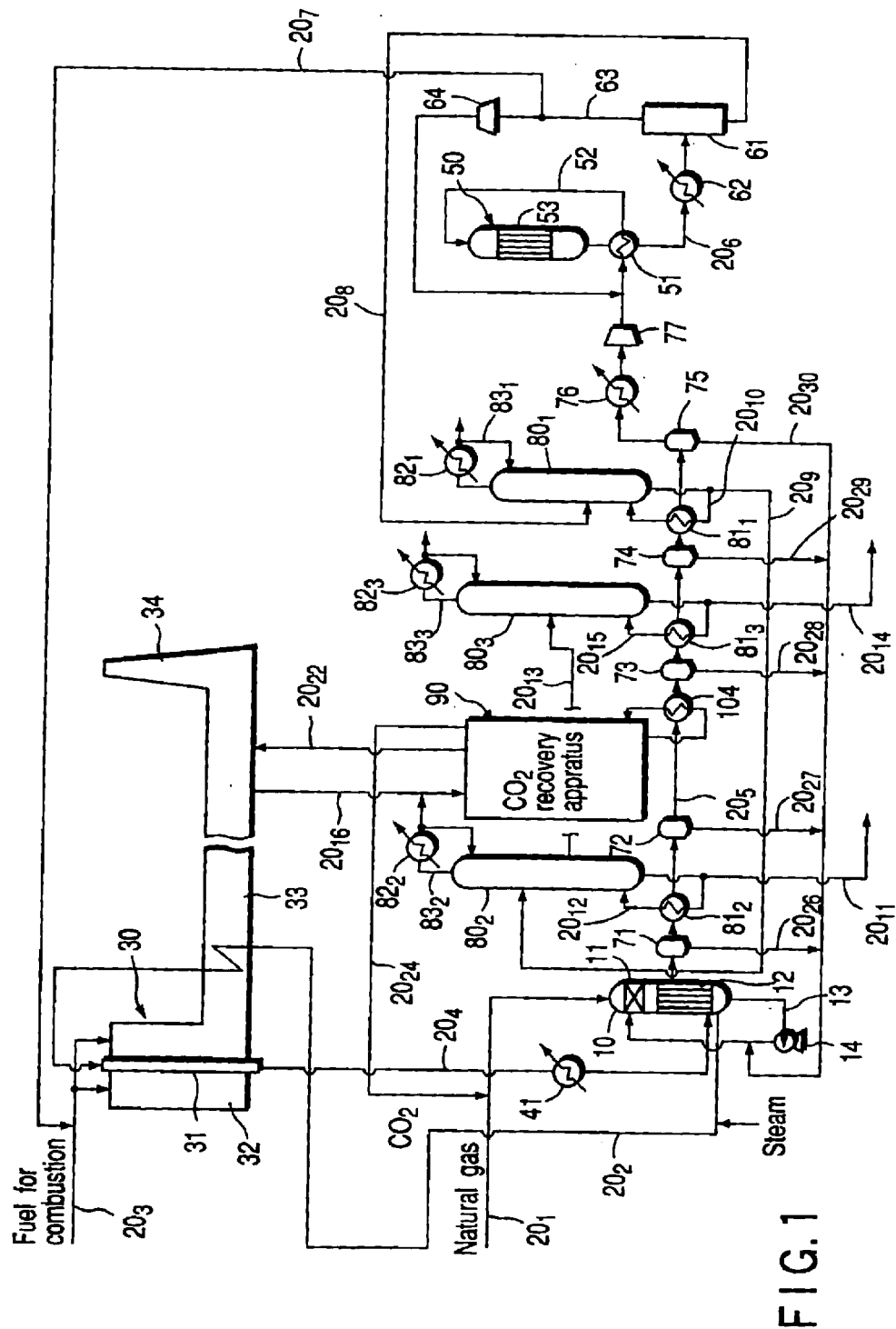
FIG. 1 is a flow chart schematically illustrating one example of the plant for manufacturing methanol according to the present invention.
Figure 2:
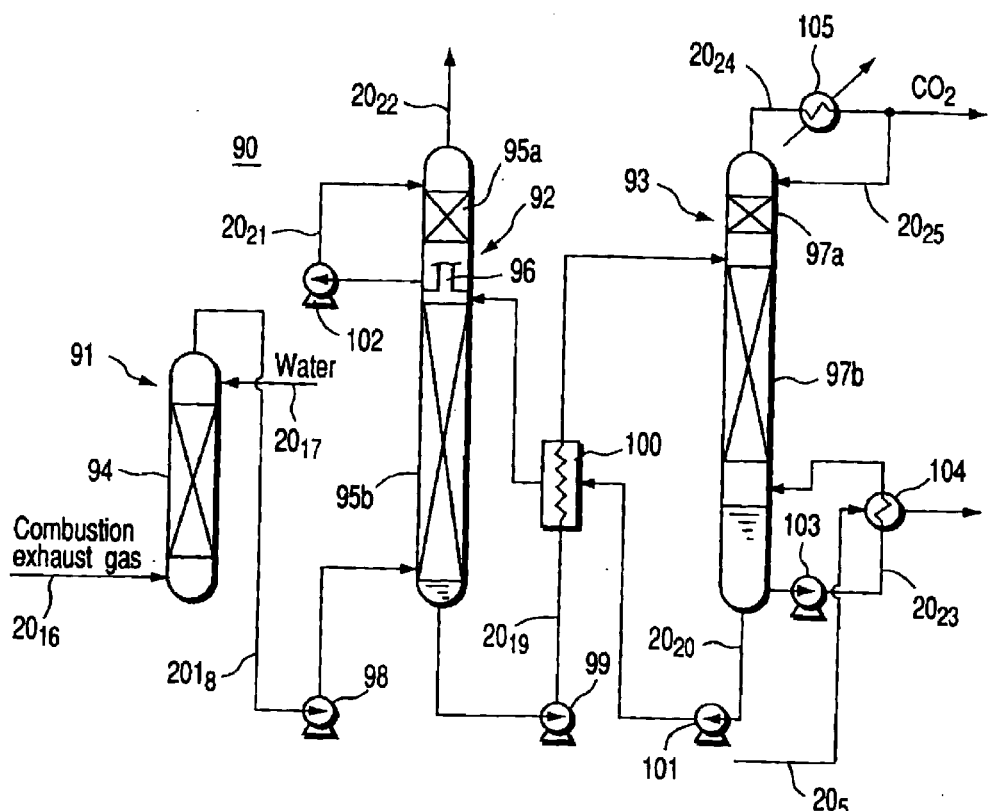
FIG. 2 is a flow chart schematically illustrating the carbon dioxide recovery apparatus to be incorporated into the methanol manufacturing plant shown in FIG. 1.

FIG. 1 schematically illustrates one example of the plant for manufacturing methanol, which was employed in the manufacture of a synthesis gas and in the manufacture of methanol using this synthesis gas; and FIG. 2 illustrates the carbon dioxide recovery apparatus shown in FIG. 1.

A single stage heat exchanger type moistening device 10 is provided therein with a filler layer 11 which is disposed close to the top of the moistening device 10, and with a tube 12 of wetted-wall type which is disposed below the filler layer 11 for contacting gas with water. A pump 14 for circulating water from the bottom of the moistening device 10 via a water circulating passageway 13 to the top of the moistening device 10 is disposed below the moistening device 10. A raw gas-feeding passageway 201 is connected with the top of the moistening device 10. This raw gas-feeding passageway $20_1$ may be provided with a desulfurizing device (not shown).

A reformer 30 is disposed on the downstream side of the moistening device 10 and connected through a passageway $20_2$ with the moistening device 10. This reformer 30 is provided with a steam-reforming reaction tube 31, a combustion device 32 which is disposed to surround the reaction tube 31 so as to heat the reaction tube 31 through the combustion of a fuel, and a chimney 34 which is communicated through a convection portion (waste heat recovery portion) 33 with the combustion device 32. The reaction tube 31 is filled with a nickel-based catalyst. A fuel-feeding passageway $20_3$ is connected with the combustion device 32 of the reformer 30.

The reaction tube 31 of the reformer 30 is connected, via a passageway $20_4$ for passing a hot synthesis gas generated in the reaction tube 31, with the moistening device 10. The passageway $20_4$ is provided with a heat exchanger 41. The moistening device 10 is connected through a passageway 205 for passing hot synthesis gas with a methanol-synthesizing reaction apparatus 50. This reaction apparatus 50 is provided with a preheater 51 and also with a methanol synthesizing reactor 53 to which a synthesis gas is fed via a circulating passageway 52 from the preheater 51. This methanol synthesizing reactor 53 is filled with a methanol-synthesizing catalyst.

A gas-liquid separator 61 is connected through a passageway $20_6$ with the preheater 51. The passageway $20_6$ is provided with a cooler 62. The gas-liquid separator 61 is connected through a gas-circulating passageway 63 with a region of the passageway $20_5$ which is located close to the inlet of the preheater 51. The gas-circulating passageway 63 is provided with a gas compressor 64. A purge gas passageway $20_7$ is branched from a region of the gas-circulating passageway 63 which is located between the gas-liquid separator 61 and the gas compressor 64, and is connected with the fuel-feeding passageway $20_3$. The crude methanol that has been separated by the gas-liquid separator 61 is permitted to enter, via a passageway $20_8$, into a first distillation tower of a distillation apparatus to be explained hereinafter.

The distillation apparatus comprises first to third distillation towers $80_1$, $80_2$ and $80_3$. The passageway $20_5$ is provided with a plurality of heat exchangers and a plurality of condensers, i.e. a first condenser 71, a heat exchanger $81_2$ of the second distillation tower $80_2$, a second condenser 72, a carbon dioxide-absorbing liquid regenerating tower heat exchanger 104 of a carbon dioxide recovery apparatus 90, a third condenser 73, a heat exchanger $81_3$ of the third distillation tower $80_3$, a fourth condenser 74, a heat exchanger $81_1$ of the first distillation tower $80_1$, a fifth condenser 75, a cooling heat exchanger 76, and a compressor 77, all of which are arranged in the mentioned order starting from the moistening device 10.

The first distillation tower $80_1$ is disposed on the downstream side of the gas-liquid separator 61 and connected via the passageway $20_8$ with the gas-liquid separator 61. A first condenser $82_1$ is connected through a circulating passageway $83_1$ with a top portion of the first distillation tower $80_1$. The bottom of the first distillation tower $80_1$ is connected via a passageway $20_9$ with the second distillation tower $80_2$. A first distillation-heating passageway $20_{10}$ is branched from a region of the passageway $20_9$ which is located close to the bottom of the first distillation tower $80_1$, and is connected via the heat exchanger $81_1$ with a lower portion of the first distillation tower $80_1$.

The second distillation tower $80_2$ is disposed on the downstream side of the first distillation tower $80_1$ and connected via the passageway $20_9$ with the first distillation tower $80_1$. A second condenser $82_2$ is connected through a circulating passageway $83_2$ with a top portion of the second distillation tower $80_2$. The bottom of the second distillation tower $80_2$ is connected with a waste water-discharging passageway $20_{11}$. A second distillation tower-heating passageway $20_{12}$ is branched from a region of the passageway $20_{11}$ which is located close to the bottom of the second distillation tower $80_2$, and is connected via the heat exchanger $81_2$ with a lower portion of the second distillation tower $80_2$.

The third distillation tower $80_3$ is disposed on the downstream side of the second distillation tower $80_2$ and connected via a passageway $20_{13}$ with the second distillation tower $80_2$. A third condenser $82_3$ is connected through a circulating passageway $83_3$ with a top portion of the third distillation tower $80_3$. The bottom of the third distillation tower $80_3$ is connected with a waste water-discharging passageway $20_{14}$. A third distillation tower-heating passageway $20_{15}$ is branched from a region of the passageway $20_{14}$ which is located close to the bottom of the third distillation tower $80_3$, and is connected via the heat exchanger $81_3$ with a lower portion of the third distillation tower $80_3$.

The carbon dioxide recovery apparatus 90 is connected through a combustion exhaust gas-feeding passageway $20_{16}$ with the convection portion 33 of the reformer 30. This carbon dioxide recovery apparatus 90 is provided as shown in FIG. 2 with a cooling tower 91, a carbon dioxide absorption tower 92 and a carbon dioxide-absorbing liquid regenerating tower 93, all of which are arranged neighboring each other. The cooling tower 91 is provided therein with a gas-liquid contacting member 94. The carbon dioxide absorption tower 92 is provided therein with a couple of upper and lower gas-liquid contacting members 95a and 95b, between which an overflow portion 96 for a regenerated carbon dioxide-absorbing liquid is disposed. The absorbing liquid regenerating tower 93 is provided therein with a couple of upper and lower gas-liquid contacting members 97a and 97b.

The cooling tower 91 is connected via the combustion exhaust gas-feeding passageway $20_{16}$ with the convection portion 33. It is designed such that the cooling water can be sprayed onto an upper portion of the cooling tower 91 through a passageway $20_{17}$, and that the combustion exhaust gas that has been introduced through the combustion exhaust gas-feeding passageway $20_{16}$ into the cooling tower 91 is cooled by the gas-liquid contacting member 94.

The top portion of the cooling tower 91 is connected via a passageway $20_{18}$ with a lower portion of the carbon dioxide absorption tower 92, and this passageway $20_{18}$ is provided with a blower 98. The bottom of the carbon dioxide absorption tower 92 is connected through a passageway $20_{19}$ with an upper portion of the absorbing liquid regenerating tower 93 which is located between the upper and lower gas-liquid contacting members 97a and 97b. A pump 99 and a heat exchanger 100 are successively mounted on the passageway $20_{19}$, the pump 99 being located closer to the carbon dioxide absorption tower 92 than the heat exchanger 100.

The bottom of the absorbing liquid regenerating tower 93 is connected through a passageway $20_{20}$ with an upper portion of the carbon dioxide absorption tower 92 where an overflow portion 96 is located, the passageway $20_{20}$ being provided so as to pass through a heat exchanger 100. A pump 101 is mounted on a region of the passageway $20_{20}$ which is located between the bottom of the absorbing liquid regenerating tower 93 and the heat exchanger 100. A passageway $20_{21}$ is communicated with the carbon dioxide absorption tower 92 in such a way that one end thereof is connected with the overflow portion 96 of the carbon dioxide absorption tower 92 and the other end thereof is connected via a pump 102 with a region of the carbon dioxide absorption tower 92 which is located over the upper gas-liquid contacting member 95a. An exhaust passageway $20_{22}$ is connected, through one end thereof, with a top portion of the carbon dioxide absorption tower 92. A passageway $20_{23}$ is connected through one end thereof with a lower portion of the absorbing liquid regenerating tower 93, the other end thereof being connected with a region of the absorbing liquid regenerating tower 93 which is located immediately below the lower gas-liquid contacting member 97b. A pump 103 and a heat exchanger 104 are arranged in the mentioned order on the passageway $20_{23}$. The heat exchanger 104 is intersected with the passageway $20_5$ so as to heat-exchange with the hot synthesis. A passageway $20_{24}$ is connected through one end thereof with a top portion of the absorbing liquid regenerating tower 93 and also connected through the other end thereof and via a cooling heat exchanger 105 with the passageway $20_2$ disposed for feeding a steam-mixed raw gas. This passageway $20_{24}$ may be provided with a compressor for compressing carbon dioxide passing therethrough. A passageway $20_{25}$ is connected through one end thereof with an upper portion of the absorbing liquid regenerating tower 93, which is located immediately over the upper gas-liquid contacting member 97a, the other end thereof being connected with a region of the passageway $20_{24}$ which is located on the downstream side of the cooling heat exchanger 105.

Further, the first, second, third, fourth and fifth condensers 71–75 are connected, through passageways $20_{26}$–$20_{30}$, with the circulating water passageway 13 of the moistening device 10. Owing to this connecting system, the condensed water to be obtained in these first-fifth condensers 71–75 can be fed to the moistening device 10 and utilized for humidifying the natural gas therein.

Next, a method of manufacturing a synthesis gas and a method of manufacturing methanol using this synthesis gas will be explained with reference to the methanol manufacturing plant shown in FIGS. 1 and 2.

1) Synthesis Gas Producing Step:

First of all, a fuel for combustion, e.g. natural gas is fed through the fuel feeding passageway $20_3$ to the combustion device 32 of the reformer 30. A portion of unreacted gas, which is generated from the gas-liquid separator 61 and is mainly containing hydrogen, is fed as purge gas, through the purge gas passageway $20_7$, to the combustion device 32 of the reformer 30. In this combustion device 32, the aforementioned natural gas and purge gas are allowed to combust together with air to thereby heat the interior of the reaction tube 31 up to a sufficiently high temperature, e.g. 850 to 900° C. The reason for heating the reaction tube 31 to such a high temperature is due to the fact that the reforming reaction inside the reformer 30 is an endothermic reaction. The combustion exhaust gas containing carbon dioxide that has been generated in the combustion device 32 is transferred through the convection portion 33 to the chimney 34. This combustion exhaust gas is cooled, as it passes through the convection portion 33, by the heat exchange thereof with a raw gas, e.g. natural gas passing through the raw gas-feeding passageway $20_2$ and mixed with steam as well as by the heat exchange thereof with boiler water (not shown).

The combustion exhaust gas cooled in the convection portion 33 is fed through the combustion exhaust gas-feeding passageway $20_{16}$ to the cooling tower 91 of the carbon dioxide recovery apparatus 90 shown in FIG. 2, and is further cooled at the gas-liquid contacting member 94 by cooling water which is fed through the passageway $20_{17}$. The combustion exhaust gas thus cooled is fed through the passageway $20_{18}$ to a lower portion of the carbon dioxide absorption tower 92 from a top portion of the cooling tower 91 by the actuation of the blower 98. During the period this combustion exhaust gas is being moved upward through the lower gas-liquid contacting member 95b disposed inside the carbon dioxide absorption tower 92, the carbon dioxide included in the combustion exhaust gas is permitted to contact with a regenerating absorbing liquid, e.g. a regenerating amine liquid, that has been fed from the absorbing liquid regenerating tower 93 through the passageway $20_{20}$ (which passes through the heat exchanger 100) to the overflow portion 96 of the carbon dioxide absorption tower 92, thereby allowing the carbon dioxide to be absorbed by the amine liquid. Further, during the period this combustion exhaust gas is being moved upward through the upper gas-liquid contacting member 95a after passing through the overflow portion 96, unabsorbed carbon dioxide remaining in the combustion exhaust gas is permitted to contact with a regenerating amine liquid that has been fed through the passageway $20_{21}$ to a top portion of the carbon dioxide absorption tower 92 by the actuation of the pump 102, thereby allowing the unabsorbed carbon dioxide to be absorbed by the amine liquid. The combustion exhaust gas thus eliminated of carbon dioxide is permitted to return, via the exhaust passageway $20_{22}$, to the convection portion 33 of the reformer 30 and discharged out of the system through the chimney 34.

The carbon dioxide-absorbed amine liquid is stored at the bottom portion of the carbon dioxide absorption tower 92. The amine liquid thus stored is enabled, by the actuation of the pump 99, to be fed therefrom and via the passageway $20_{19}$ to an upper portion of the absorbing liquid regenerating tower 93, which is located between a couple of the upper and lower gas-liquid contacting members 97a and 97b disposed inside the absorbing liquid regenerating tower 93. In this case, during the period this carbon dioxide-absorbed amine liquid is being passed through the heat exchanger 100 mounted on the passageway $20_{19}$, the amine liquid is heat-exchanged with a regenerated amine liquid having a relatively high temperature and passing through the passageway $20_{20}$ which is connected with the bottom of the absorbing liquid regenerating tower 93, thereby heating up the carbon dioxide-absorbed amine liquid and at the same time, cooling the regenerated amine liquid passing through the passageway $20_{20}$ and having a relatively high temperature. The carbon dioxide-absorbed amine liquid which has been heated up in this manner is then separated into carbon dioxide and regenerated amine liquid during the period the carbon dioxide-absorbed amine liquid flows down through the lower gas-liquid contacting member 97b of the heated absorbing liquid regenerating tower 93. On this occasion, the regenerated amine liquid is stored in the bottom of the regenerating tower 93 and permitted to circulate through the passageway $20_{23}$ as the pump 103 is actuated, during which the regenerated amine liquid is heat-exchanged at the heat exchanger 104 which is intersected with the passageway $20_5$ through which a hot synthesis gas having a high temperature is permitted to pass as explained hereinafter. The regenerated amine liquid heated in this manner is utilized to heat the absorbing liquid regenerating tower 93 itself, thereby rendering the regenerated amine liquid to be utilized as a heat source for separating the carbon dioxide-absorbed amine liquid into carbon dioxide and regenerated amine liquid.

The regenerated amine liquid which has been separated in this manner is stored at the bottom of the regenerating tower 93 and then returned through the passageway $20_{20}$ to the carbon dioxide absorption tower 92 by the actuation of the pump 101. On the other hand, the carbon dioxide that has been separated from the carbon dioxide-absorbed amine liquid is permitted to flow upward through the upper gas-liquid contacting member 97a of the regenerating tower 93 and circulated through the circulating passageway $20_{24}$ from a top portion of the absorbing liquid regenerating tower 93, during which the carbon dioxide is cooled by the cooling heat exchanger 105, thereby condensing the amine vapor which is being carried together the carbon dioxide, the condensed amine liquid being subsequently permitted to return to the absorbing liquid regenerating tower 93 through the branched passageway $20_{25}$. The carbon dioxide thus recovered is fed through the passageway $20_{24}$ to the passageway $20_1$ disposed for passing natural gas as described hereinafter.

As a raw gas, e.g. natural gas mainly consisted of hydrocarbons that have been desulfurized by a desulfurizer (not shown) passes through the raw gas-feeding passageway $20_1$, a predetermined quantity of carbon dioxide that has been recovered by the carbon dioxide recovery apparatus 90 is added, by way of the passageway $20_{24}$, to the raw gas and mixed therewith. This mixed gas comprising the natural gas and carbon dioxide is then transferred through the raw material-feeding passageway $20_1$ toward the filler layer 11 disposed at a top portion of the heat exchanger type moistening device 10. In this case, the pump 14 which is disposed below the heat exchanger type moistening device 10 is actuated in advance to enable water to circulate from the bottom of the heat exchanger type moistening device 10 to the top portion of the heat exchanger type moistening device 10 through the circulating water passageway 13, thus moistening the mixed gas comprising the natural gas and carbon dioxide that has been introduced into the top portion of the heat exchanger type moistening device 10. After the mixed gas has been contacted with and moistened by the water that has been supplied from the circulating water passageway 13 at the filler layer 11, the mixed gas is further heated and moistened through the heat exchange thereof at the tube 12 with a hot synthesis gas that has been supplied thereto from the reformer 30 through the passageway $20_4$. As a result, water vapor (steam) is substantially added to the mixed gas.

By the way, it is preferable, on the occasion of mixing the natural gas with carbon dioxide and steam, to set the mixing ratio of methane ($CH_4$) in the natural gas:steam ($H_2O$) to 1:1.5–1:5 (based on molar ratio), and the mixing ratio of methane ($CH_4$):carbon dioxide ($CO_2$) to 1:0.1–1:3 (based on molar ratio).

The natural gas incorporated with carbon dioxide and steam is permitted to pass through the passageway $20_2$ and then, pre-heated during the period the natural gas is permitted to pass through the convection portion 33 of the reformer 30, after which the natural gas is fed to the reaction tube 31 which has been heated up to a sufficient temperature.

All of these steam, carbon dioxide and natural gas consisting mainly of methane ($CH_4$) that have been fed to the reaction tube 31 of the reformer 30 are allowed to react with each other in the presence of a catalyst in the reaction tube 31, wherein the steam-reforming of methane is allowed to take place, thus producing a synthesis gas comprising hydrogen, carbon monoxide and carbon dioxide according to the following formulas (1) and (2).

$$CH_4 + H_2O \rightleftarrows CO + 3H_2 \quad (1)$$

$$CO + H_2O \rightleftarrows CO_2 + H_2 \quad (2)$$

As seen from these formulas (1) and (2) of reforming reaction, as a result of the reaction between one mole of methane and two moles of steam, four moles of hydrogen and one mole of carbon dioxide are produced. In the actual reaction system however, a composition which is close to the chemical reaction equilibrium composition that will be determined by the outlet temperature and pressure of the reaction tube 11 can be obtained.

2) Heat Exchange and Cooling Step of Hot Synthesis Gas:

The hot synthesis gas produced at the reformer 30 is transferred via the passageway $20_4$ to the heat exchanger 41, wherein the hot synthesis gas is used for heating boiler water to generate a high-pressure steam, and at the same, the hot synthesis gas itself is cooled and then fed to an outer passageway of the tube 12 of the moistening device 10. In this tube 12, part of the heat of the synthesis gas is recovered and utilized as a heat source for the moistening device 10.

The synthesis gas passed through the moistening device 10 is fed via the passageway $20_5$ to the methanol-synthesizing reaction apparatus 50 as shown in FIG. 1. On this occasion, during the period this synthesis gas passes through the passageway $20_5$, this synthesis gas is cooled through the heat exchange thereof with the heat exchanger $81_2$ of the second distillation tower $80_2$, with the carbon dioxide-absorbing liquid regenerating tower heat exchanger 104 of a carbon dioxide recovery apparatus 90, with the heat exchanger $81_3$ of a third distillation tower $80_3$, and with the heat exchanger $81_1$ of the first distillation tower $80_1$. The synthesis gas thus cooled is further cooled by the cooling heat exchanger 76 and then pressurized, by means of the compressor 77, up to a pressure (for example, 50–150 atm) which is suited for the methanol synthesizing reaction. Namely, the waste heat of the synthesis gas is effectively utilized during the processes the synthesis gas passes through the aforementioned heat exchangers $81_1$–$81_3$ and 104, thus allowing synthesis gas itself to be cooled in these processes. Further, the water vapor included in the synthesis gas is turned into condensed water by the first, second, third, fourth and fifth condensers 71–75, the condensed water being subsequently fed, through passageways $20_{26}$–$20_{30}$, to the circulating water passageway 13 of the moistening device 10, thereby enabling the condensed water to be utilized in moistening the raw gas that has been introduced into the moistening device 10.

3) Crude Methanol Synthesizing Step:

The synthesis gas pressurized is fed through the passageway $20_5$ to the preheater 51 of the methanol synthesizing reaction apparatus 50, in which the synthesis gas is preheated up to a temperature (for example, 200–300° C.) which is suited for the methanol synthesis reaction. Thereafter, the preheated synthesis gas is fed through the circulating passageway 52 to the methanol synthesizing reactor 53 which is filled with methanol synthesis catalyst. By the way, the unreacted gas which has been separated at the gas-liquid separator 61 (to be explained hereinafter) is fed through the gas circulating passageway 63 to a region of the passageway 205 which is located immediately before the preheater 51, thereby enabling the unreacted gas to be mixed with the synthesis gas. In the reactor 53, a product containing methanol that has been synthesized according to the reactions as shown in the following formulas (3) and (4) can be obtained.

$$CO + 2H_2 \rightleftarrows CH_3OH \quad (3)$$

$$CO_2 + 3H_2 \rightleftarrows CH_3OH + H_2O \quad (4)$$

Furthermore, due to side reactions, impurities such as dimethyl ether and ethanol are produced. These impurities and water are existed together with methanol in the product to form a liquid crude methanol.

4) Liquid Crude Methanol Recovering Step:

The product obtained from the reactor 53 is successively fed through the circulating passageway 52 and the passageway $20_6$ to the cooler 62 so as to be cooled down to ordinary temperature. At this moment, most of the methanol and steam contained in the product are condensed and permitted to enter as a liquid into the gas-liquid separator 61. In this gas-liquid separator 61, the product is separated into a liquid crude methanol and an unreacted gas, i.e. hydrogen-rich unreacted gas mainly consisting of hydrogen.

Most of this hydrogen-rich unreacted gas is then fed through the gas circulating passageway 63 to the gas compressor 64, in which the hydrogen-rich unreacted gas is compressed and then circulated through the gas circulating passageway 63 to a region of the passageway 205 which is located at the inlet of the preheater 51 so as to be fed together with the synthesis gas to the reactor 53. Part of the hydrogen-rich unreacted gas is employed as a purge gas and passed through the purge gas passageway 207 so as to be utilized as part of the fuel for the combustion device 32 in the reformer 30.

5) Distillation Step:

The liquid crude methanol which has been separated by the gas-liquid separator 61 is fed through the passageway $20_8$ to the first distillation tower $80_1$ of the distillation apparatus. This liquid crude methanol is then heated by making the most of the heat that has been generated by the heat-exchange at the heat exchanger $81_1$ with the waste heat of the hot synthesis gas passing through the passageway $20_5$. Low boiling point organic compounds are concentrated at a top portion of the first distillation tower $80_1$, and part of the low boiling point organic compounds is condensed at the first condenser $82_1$ and refluxed, the balance thereof being discharged out of the system together with dissolved gases.

The bottom liquid (mainly consisting of methanol and water) of the first distillation tower $80_1$ is fed through the passageway $20_9$ to the second distillation tower $80_2$. The methanol and water that have been introduced into the second distillation tower $80_2$ are heated by making the most of the heat that has been generated by the heat-exchange at the heat exchanger $81_2$ with the waste heat of the hot synthesis gas passing through the passageway $20_5$. At the top portion of the second distillation tower $80_2$, a methanol fraction is cooled and condensed by the second condenser $82_2$, the condensed methanol fraction being subsequently refluxed and refined to produce high purity methanol which is then taken out of the system. The bottom liquid of the second distillation tower $80_2$ is mainly consisted of water, but also contains a small quantity of high-boiling point organic compounds and organic acids, as well as a minute amount of inorganic matters originating from the apparatus, this waste water being subsequently taken out of the bottom of the second distillation tower $80_2$ and discharged out of the system through the passageway $20_{11}$.

A liquid mainly containing unrefined methanol is left remain near the center portion of the second distillation tower $80_2$, this unrefined methanol being subsequently transferred via the passageway $20_{13}$ to the third distillation tower $80_3$. The liquid that has been introduced into the third distillation tower $80_3$ is heated by making the most of the heat that has been generated by the heat-exchange at the heat exchanger $81_3$ with the waste heat of the hot synthesis gas passing through the passageway $20_5$. At the top portion of the third distillation tower $80_3$, a methanol fraction is cooled and condensed by the third condenser $82_3$, the condensed methanol fraction being subsequently refluxed and refined to produce high purity methanol which is then taken out of the system. The bottom liquid of the third distillation tower $80_3$ is a waste water mainly consisted of water and subsequently taken out of the bottom of the third distillation tower $80_3$ and discharged out of the system through the passageway $20_{14}$.

As described above, according to the present invention, it is possible, through the addition of carbon dioxide together with steam to natural gas, to manufacture a synthesis gas having an $H_2/(CO+CO_2)$ ratio which is suited for synthesizing methanol.

Further, since the combustion exhaust gas discharged from the reformer 30 is recovered by the carbon dioxide recovery apparatus 90 so as to utilize the carbon dioxide contained therein as one component of the raw gas for the manufacture of synthesis gas, the quantity of carbon dioxide to be discharged out of the system in the manufacture of synthesis gas can be reduced. As a result, the economy of methanol manufacturing plant can be improved particularly when the tax to the emission of carbon dioxide is newly introduced or when a more severe regulation for the emission of carbon dioxide is newly enforced.

Further, since the waste heat of the hot synthesis gas generated in the reformer 30 is utilized as a heat source for the carbon dioxide-absorbing liquid-regenerating tower 93 of the carbon dioxide recovery apparatus 90, it becomes possible to reduce the thermal energy required in the production of a synthesis gas and to reduce the manufacturing cost of the synthesis gas.

Furthermore, since the waste heat of the hot synthesis gas generated in the reformer 30 is utilized as a heat source for the carbon dioxide-absorbing liquid-regenerating tower 93 of the carbon dioxide recovery apparatus 90 and also as a heat source for the first, second and third distillation towers $80_1$, $80_2$ and $80_3$, it becomes possible to cool the synthesis gas down to a sufficiently low temperature and to reduce the thermal energy required in the production of methanol. As a result, it is now possible to reduce the manufacturing cost of methanol.

In particular, as shown in FIG. 1, the heat exchangers $81_1$–$81_3$ of the first, second and third distillation towers $80_1$–$80_3$ are mounted on and along the passageway $20_5$ in such a manner that the heat exchanger $81_2$ of the second distillation tower $80_2$ which is required to be heated at a highest temperature is disposed at first, which is followed successively on the downstream side thereof by the heat exchanger 104 of the absorbing liquid regenerating tower 93, by the heat exchanger $81_3$ of the third distillation tower $80_3$, and by the heat exchanger $81_1$ of the first distillation tower $80_1$. Due to this arrangement, the setting of temperature conditions of the first, second and third distillation towers $80_1$–$80_3$ can be easily executed so as to optimize them for the refining of liquid crude methanol, and also the setting of temperature condition of the regenerating tower 93 of the carbon dioxide recovery apparatus 90 can be easily executed so as to optimize it for the regeneration of the absorbing liquid.

Figure 3:
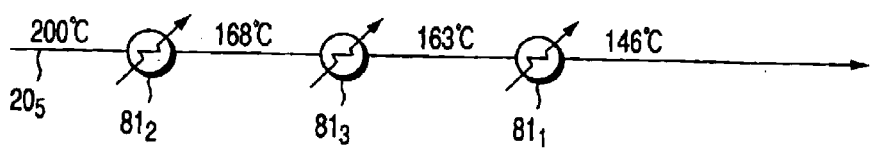
FIG. 3 is a diagram for illustrating changes in temperature of a hot synthesis gas on an occasion wherein a flow route for passing the hot synthesis gas is provided with a heat exchanger of a second distillation tower, a heat exchanger of a third distillation tower, and a heat exchanger of a first distillation tower, all of these heat exchangers being successively arranged in the mentioned order, thereby enabling the hot synthesis gas to successively undergo the heat exchange thereof.

In fact, when the heat exchange of synthesis gas was performed under the condition wherein the heat exchanger $81_2$ of the second distillation tower $80_2$, the heat exchanger $81_3$ of the third distillation tower $80_3$ and the heat exchanger $81_1$ of the first distillation tower $80_1$ were arranged in the mentioned order on the passageway $20_5$ as shown in FIG. 3, the temperature of the synthesis gas passing through the passageway $20_5$ was lowered at most to 146° C. Whereas, when the heat exchange of synthesis gas was performed under the condition wherein the heat exchanger $81_2$ of the second distillation tower $80_2$, the heat exchanger 104 of the absorbing liquid regenerating tower 93, the heat exchanger $81_3$ of the third distillation tower $80_3$ and the heat exchanger $81_1$ of the first distillation tower $80_1$ were arranged in the mentioned order on the passageway $20_5$ as shown in FIG. 4, it was possible to lower the temperature of the synthesis gas passing through the passageway $20_5$ to as low as 96° C., thus demonstrating that the synthesis gas can be lowered to a sufficiently low temperature and that the waste heat of the synthesis gas can be effectively utilized.

Figure 4:
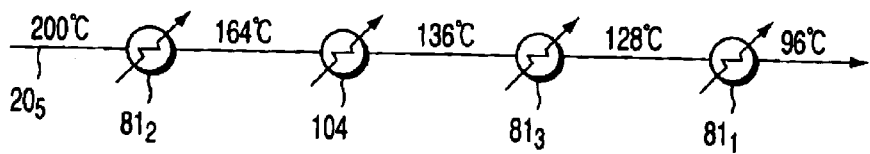
FIG. 4 is a diagram for illustrating changes in temperature of a hot synthesis gas on an occasion wherein a flow route for passing the hot synthesis gas is provided with a heat exchanger of a second distillation tower, a heat exchanger of a carbon dioxide recovery apparatus for regenerating the carbon dioxide-absorbing liquid, a heat exchanger of a third distillation tower, and a heat exchanger of a first distillation tower, all of these heat exchangers being successively arranged in the mentioned order, thereby enabling the hot synthesis gas to successively undergo the heat exchange thereof.

The ratio [a/b] of the amount of consumption of natural gas (fuel for the combustion+raw material) [a] per a unit quantity of production of methanol [b] on a case where the waste heat of synthesis gas is heat-exchanged by making use of three heat exchangers of three distillation towers (example 1) as shown in FIG. 3, and on a case where the waste heat of synthesis gas is heat-exchanged by making use of three heat exchangers of three distillation towers together with the recovery tower heat exchanger of the carbon dioxide recovery apparatus (Example 2) as shown in FIG. 4. As a result, the ratio [a/b] in the Example 2 was 94 in comparison with the ratio [a/b] in the example 1 which was assumed as being 100, thus indicating that it is possible according to the Example 2 to manufacture methanol with a lower fuel consumption, or a smaller thermal energy as compared with the example 1.

By the way, in the foregoing embodiment, the synthesis gas was employed for the manufacture of methanol, the synthesis gas can be utilized in the same manner in the manufacture of gasoline by means of GTL (Gas to Liquid) process, or in the manufacture of dimethyl ether.

As described above, according to the present invention, it is possible to provide a method of manufacturing a synthesis gas having an $H_2/(CO+CO_2)$ molar ratio which is suited for the synthesis of methanol at the reformer, and a method of manufacturing a synthesis gas wherein the waste heat generated in a reformer can be effectively utilized as a heat source for the carbon dioxide-absorbing liquid regenerating tower of the carbon dioxide recovery apparatus, thereby making it possible to reduce the energy consumption and to lower the manufacturing cost thereof.

Furthermore, according to the present invention, it is possible to produce a synthesis gas having an $H_2/(CO+CO_2)$ molar ratio which is suited for the synthesis of methanol at the reformer, and at the same time, to provide a method of manufacturing methanol wherein the waste heat of the hot synthesis gas generated at the reformer can be effectively utilized as a heat source for the carbon dioxide-absorbing liquid regenerating tower of the carbon dioxide recovery apparatus and also as a heat source for the distillation apparatus, thereby making it possible to reduce the energy consumption and to lower the manufacturing cost thereof.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing a synthesis gas comprising: reacting hydrocarbons with water vapor in a reformer to produce a synthesis gas containing hydrogen, carbon monoxide and carbon dioxide; recovering carbon dioxide from combustion exhaust gas which has been discharged from said reformer by a carbon dioxide recovery apparatus provided with a carbon dioxide absorption tower and with a carbon dioxide-absorbing liquid regenerating tower; and feeding the carbon dioxide thus recovered, as a component of raw gas, to the upstream side and/or the downstream side of said reformer;

wherein the hot synthesis gas produced in the reformer is utilized as a heat source for regenerating a carbon dioxide-absorbing liquid in said carbon dioxide-absorbing liquid regenerating tower of said carbon dioxide recovery apparatus.

2. The method of manufacturing a synthesis gas according to claim 1, wherein the carbon dioxide recovered by said carbon dioxide recovery apparatus from combustion exhaust gas discharged from said reformer is mixed with the hydrocarbons to prepare a mixed gas, and the resultant mixed gas is subsequently fed to a moistening device to add water vapor to the mixed gas, the resultant moistened mixed gas being subsequently fed to said reformer to allow a reforming reaction to take place.

3. The method of manufacturing a synthesis gas according to claim 1 or 2, wherein said hydrocarbons are natural gas.

4. The method of manufacturing a synthesis gas according to claim 1, wherein said hot synthesis gas produced in the reformer is further utilized as a heat source for regenerating carbon dioxide-absorbing liquid in said carbon dioxide-absorbing liquid regenerating tower by making use of a heat exchanger.

5. A method of manufacturing methanol comprising:

reacting hydrocarbons with water vapor in a reformer to produce a synthesis gas containing hydrogen, carbon monoxide and carbon dioxide;

recovering carbon dioxide from combustion exhaust gas which has been discharged from said reformer by a carbon dioxide recovery apparatus provided with a carbon dioxide absorption tower and with a carbon dioxide-absorbing liquid regenerating tower;

feeding the carbon dioxide thus recovered, as a component of raw gas, to the upstream side and/or the downstream side of said reformer;

producing a crude methanol by introducing the synthesis gas into a methanol-synthesizing reaction apparatus; and distilling said crude methanol by making use of a distillation apparatus to produce a refined methanol;

wherein said hot synthesis gas produced in said reformer is utilized as a heat source for regenerating a carbon dioxide-absorbing liquid in said carbon dioxide-absorbing liquid regenerating tower, and said hot synthesis gas produced in said reformer is utilized as a heat source for said distillation apparatus.

6. The method of manufacturing methanol to claim 5, wherein said synthesis gas is produced by a process wherein the carbon dioxide recovered by said carbon dioxide recovery apparatus from combustion exhaust gas discharged from said reformer is mixed with the hydrocarbons to prepare a mixed gas, and the resultant mixed gas is subsequently fed to a moistening device to add water vapor to the mixed gas, the resultant moistened mixed gas being subsequently fed to said reformer to allow a reforming reaction to take place.

7. The method of manufacturing methanol according to claim 5, wherein said hydrocarbons are natural gas.

8. The method of manufacturing methanol according to claim 5, wherein said hot synthesis gas produced in said reformer is further utilized as a heat source for regenerating carbon dioxide-absorbing liquid in said carbon dioxide-absorbing liquid regenerating tower by making use of a heat exchanger.

9. The method of manufacturing methanol according to claim 5 or 8, wherein said hot synthesis gas produced in said reformer is further utilized as a heat source for said distillation apparatus by making use of a heat exchanger.

10. The method of manufacturing methanol according to claim 7 or 8, wherein said distillation apparatus is provided with a first, a second and a third distillation towers each provided with a heat exchanger, thereby enabling said hot synthesis gas from said reformer to pass successively through said heat exchanger of said second distillation tower, said heat exchanger of said carbon dioxide-absorbing liquid regenerating tower, said heat exchanger of said third distillation tower, and said heat exchanger of said first distillation tower, thus enabling the hot synthesis gas to successively undergo the heat exchange thereof.

* * * * *